United States Patent [19]

Breitscheidel et al.

[11] Patent Number: 5,536,691
[45] Date of Patent: Jul. 16, 1996

[54] COBALT CATALYSTS AND A PROCESS REQUIRED FOR THEIR PREPARATION

[75] Inventors: Boris Breitscheidel, Fulda; Peter Polanek, Weinheim; Matthias Irgang, Heidelberg; Hermann Petersen, Gruenstadt; Gerd Linden, Heidelberg; Guido Voit, Schriesheim; Tom Witzel, Ludwigshafen, all of Germany

[73] Assignee: BASF Aktiengesellschaft, Ludwigshafen, Germany

[21] Appl. No.: 269,060

[22] Filed: Jun. 30, 1994

[30] Foreign Application Priority Data

Jul. 31, 1993 [DE] Germany .................. 43 25 847.6

[51] Int. Cl.⁶ .................. B01J 23/04; B01J 23/34; B01J 23/78
[52] U.S. Cl. .................. 502/213; 502/324; 502/325; 502/344
[58] Field of Search .................. 502/213, 324, 502/330, 344, 325

[56] References Cited

U.S. PATENT DOCUMENTS

| | | | |
|---|---|---|---|
| 4,447,558 | 5/1984 | Sasaki et al. | 502/215 |
| 4,598,058 | 7/1986 | Frank et al. | |
| 5,183,793 | 2/1993 | Paparizos et al. | 502/330 |
| 5,254,738 | 7/1992 | Koehler et al. | |

FOREIGN PATENT DOCUMENTS 0383132  2/1990  European Pat. Off. .

*Primary Examiner*—Anthony McFarlane
*Attorney, Agent, or Firm*—John H. Shurtleff

[57] ABSTRACT

Cobalt catalysts whose catalytically active material comprises from 55 to 98 wt % of cobalt, from 0.2 to 15 wt % of phosphorus, from 0.2 to 15 wt % of manganese, and from 0.2 to 15 wt % of alkali metal, calculated as oxide, in which the catalyst material is calcined in a first step at final temperatures of from 550° to 750° C. and in a second step at final temperatures of from 800° to 1000° C., and a process for the hydrogenation of organic nitriles and/or imines, in which the novel cobalt catalyst is used.

9 Claims, No Drawings

COBALT CATALYSTS AND A PROCESS REQUIRED FOR THEIR PREPARATION

The present invention relates to novel cobalt catalysts whose catalytically active material comprises cobalt, phosphorus, manganese and alkali metal and which are prepared via two calcination steps at final temperatures of from 550° to 750° C. and from 800° to 1000° C. respectively.

EP-A 445,589 discloses hydrogenation catalysts whose catalytically active material contains from 20 to 95 wt % of cobalt oxide, from 0.5 to 60 wt % of oxides of the metals manganese, nickel, iron, chromium, molybdenum, tungsten or phosphorus and from 0.5 to 20 wt % of oxides of the alkali metal group or the alkaline earth metal group or the rare earth group scandium or yttrium.

DE-A 3,403,377 discloses shaped catalyst materials, which contain metallic cobalt and/or nickel having a content of less than 0.1 wt % of alkali metal oxides and/or alkaline earth metal oxides, and which are prepared at temperatures of 500° C. or less by reduction. The shaped catalyst materials have a compression hardness of more than 300 kp/cm².

However the catalysts mentioned above have the drawback that they are not sufficiently inert to bases to guarantee a long service life in basic medium.

It was thus the object of the present invention to overcome the aforementioned drawbacks.

Accordingly, we have found a novel and improved cobalt catalyst whose catalytically active material consists of from 55 to 98 wt % of cobalt, from 0.2 to 15 wt % of phosphorus, from 0.2 to 15 wt % of manganese and from 0.2 to 15 wt % of alkali metal, calculated as oxide, wherein the catalyst material is calcined in a first step at final temperatures of from 550° to 750° C. and in a second step at final temperatures of from 800° to 1000° C., and a process for the hydrogenation of organic nitriles and/or imines in which the said novel cobalt catalyst is used.

The catalytically active material of the cobalt catalysts of the invention consists of from 55 to 98 wt % of cobalt, preferably from 75 to 95 wt % of cobalt and more preferably from 85 to 95 wt % of cobalt, from 0.2 to 15 wt % of phosphorus, preferably from 0.5 to 10 wt % of phosphorus and more preferably from 0.5 to 5 wt % of phosphorus, from 0.2 to 15 wt % of manganese, preferably from 2 to 10 wt % of manganese and more preferably from 3 to 7 wt % of manganese and from 0.2 to 15 wt % of alkali metal, preferably from 0.5 to 5 wt % of alkali metal and more preferably from 0.5 to 4 wt % of alkali metal, calculated as oxide.

Suitable alkali metals are preferably lithium, sodium, potassium and/or cesium and more preferably sodium and/or potassium.

The cobalt catalysts of the invention can be prepared as follows:

A solution of a cobalt salt, preferably of an inorganic cobalt salt and optionally of the desired promotors manganese, phosphorus and/or alkali metals in the form of their water-soluble salts (pH normally <7) can be precipitated by adding an alkaline solution of a mixture of the main constituents contained in the catalyst in the form of their carbonates, hydroxides or oxides. The alkaline solution can be prepared by dissolving, e.g, alkali metal carbonates or hydroxides, ammonia, ammonium carbonate or ammonium bicarbonate or similar basic salts in water. The concentrations of both the metal salt and the precipitating solution should be adjusted such that the resulting precipitate can still be stirred. If the promotors are not co-precipitated in this step, they can be added in a process step described below.

The addition of the basic solution is continued until complete precipitation is achieved. The precipitate can be stirred for a further period, if necessary, isolated by filtration using conventional industrial facilities and washed free of undesirable water-soluble foreign ions.

The resulting filter cake can then be dried at temperatures of from 50° to 2000° C. and the resulting material ground. Alternatively, a slurry can be prepared which is then spray-dried in a spraying tower. In this case there is formed a powder at temperatures between 100° C. and 600° C. If the spraying method is used, the promotors manganese, phosphorus and/or alkali metals can also be added to the catalyst in this process step in the form of their salts.

The resulting powder can be calcined. The calcined powder can be shaped in various ways to produce shaped articles. Thus it is possible to pellet the powder, to extrude it or to mold it with the assistance of an extruder to produce extrudates of specific shape and size. In all of said cases shaping auxiliaries such as graphite or stearic acid can be admixed.

Calcination is carried out in at least two calcination steps, of which one is carried out at final temperatures of from 550° to 750° C. followed by another calcination step effected at final temperatures of from 800° to 1000° C. Further single-stage or multiple-stage thermal treatments can be carried out at temperatures of from 200° to 1100° C., preferably from 400° to 1000° C. and more preferably from 500° to 900° C.

There are thus obtained cobalt catalysts having a surface area of 1.5 m²/g or more, i.e., from 1.5 to 500 m²/g, preferably from 5 to 300 m²/g and more preferably from 10 to 250 m²/g.

Suitable shapes are any of the geometrical shapes capable of being used in fixed bed reactors.

Both solid and supported catalysts are suitable for hydrogenations. This applies also to the reaction of nitriles and imines with hydrogen to form the corresponding amines.

As a criterion of the long-term stability (including, e.g., the inertness to bases), a test has been developed which makes it possible to obtain a quick report on the on-stream properties of a catalyst under reaction conditions.

This short time test, which has been designated as the boiling test, can be carried out as follows:

A catalyst which has been reduced with hydrogen above 250° C. and an aqueous base such as NaOH or KOH can be placed in an autoclave under a blanket of inert gas and kept at ca 160° C. for 12 h under autogenous pressure (ca 5 bar). Following cooling, removal of the liquid by decantation, and washing of the catalyst with water, the hardness can be determined under a blanket of inert gas, e.g., nitrogen.

A catalyst having an abrasive hardness greater than or equal to 10 newton, i.e., from 10 to 1000 newton, preferably from 15 to 100 newton and more preferably from 20 to 50 newton as determined in the boiling test usually posesses an adequate long-term stability ( on-stream time >3000 h).

The cobalt catalysts of the invention are suitable for use as hydrogenation catalysts, particularly for reactions of nitriles with hydrogen to form primary amines.

EXAMPLES

Boiling Test

In an autoclave having a capacity of 250 mL and containing a teflon® (polytetrafluorothylene) insert, there were placed 10 mL of catalyst in reduced form under nitrogen and 100 mL of a 2.5% strength aqueous NaOH solution. The reduction of the catalyst was previously carried out in continuous apparatus with $H_2$ at 360° C. over a period of 5 h. The sealed autoclave was heated to 160° C. This produced an autogenous pressure of ca 5 bar. The temperature was kept at 160° C. for 12 h. Following cooling, the liquid was removed by decantation, the catalyst washed with water and then the hardness determined under $N_2$.

Preparation of the catalyst

The percentages by weight are based on the respective oxides in the annealed catalyst, the phosphorus content is given as $H_3PO_4$.

Catalyst A

By dissolving cobalt nitrate, manganese nitrate and phosphoric acid in water a solution was prepared which contained 10 wt % of cobalt, 0.55 wt % of manganese and 0.45 wt % of $H_3PO_4$. Precipitation was caused to take place by adding a 20% strength sodium carbonate solution at a temperature of 50° C. The resulting precipitate was washed until no more sodium or nitrate could be detected in the wash water. The resulting solid material was slurried with water and spray-dried in a spraying tower (input temperature =550° C.). The sprayed material was dried at 500° C., ground and shaped in an extruder to produce extrudates of 4 mm in diameter. The extrudates were dried at from 100° to 120° C. and then calcined 1 h at 650° C. and subsequently for 3 h at 850° C.

The resulting catalyst contained 90.4 wt % of cobalt, 5.1 wt % of manganese, 0.3 wt % of sodium and 3.1 wt % of phosphorus and had a specific surface area of 1.6 $m^2/g$.

Catalyst B

Preparation was carried out in a manner similar to catalyst A, except that 73 g of $H_3PO_4$ were mixed into 4 kg of sprayed powder prior to extrusion. The catalyst was calcined for 1 h at 650° C. and then for 3 h at 820° C. There was obtained a catalyst having a specific surface area of 3.2 $m^2/g$ and the following chemical composition: 89.5 wt % of cobalt, 5.05 wt % of manganese, 1.41 wt % of sodium, 4.5 wt % of phosphorus.

Catalyst C

Preparation was carried out in a manner similar to catalyst A, except that 19.8 g of NaOH were mixed into 4 kg of sprayed powder prior to extrusion. The catalyst was calcined for 1 h at 650° C. and then for 3 h at 820° C. There was obtained a catalyst having a specific surface area of 15.1 $m^2/g$ and the following chemical composition: 89.9 wt % of cobalt, 5.1 wt % of manganese, 1.9 wt % of sodium, 4.2 wt % of phosphorus.

Catalyst D

Preparation was carried out in a manner similar to catalyst A, except that 12.8 g of $H_3PO_4$ were mixed into 4 kg of sprayed powder prior to extrusion. The catalyst was calcined for 1 h at 650° C. and then for 3 h at 820° C. There was obtained a catalyst having a specific surface area of 3.0 $m^2/g$ and the following chemical composition: 90.4 wt % of cobalt, 5.1 wt % of manganese, 1.36 wt % of sodium, 2.8 wt % of phosphorus.

Catalyst E

Preparation was carried out in a manner similar to catalyst A, except that 18.3 g of NaOH were mixed into 4 kg of sprayed powder prior to extrusion. The catalyst was calcined for 1 h at 650° C. and then for 2 h at 820° C. There was obtained a catalyst having a specific surface area of 6.2 $m^2/g$ and the following chemical composition: 89.9 wt % of cobalt, 5.1 wt % of manganese, 1.9 wt % of sodium, 3.1 wt % of phosphorus.

Catalyst F (Comparative Catalyst)

Preparation was carried out in a manner similar to catalyst A, except that 73 g of $H_3PO_4$ were mixed into 4 kg of sprayed powder prior to extrusion. The catalyst was calcined for 1 h at 650° C. and then for 1 h at 780° C. There was obtained a catalyst having a specific surface area of 7.1 $m^2/g$ and the following chemical composition: 89.5 wt % of cobalt, 5.1 wt % of manganese, 1.41 wt % of sodium, 4.1 wt % of phosphorus.

Catalyst G (Comparative Catalyst)

Preparation was carried out in a manner similar to catalyst F, except that calcination was carried out for 1 h at 650° C. and then for 1 h at 840° C. There was obtained a catalyst having a specific surface area of 1.4 $m^2/g$ and the following chemical composition: 89.5 wt % of cobalt, 5.1 wt % of manganese, 1.4 wt % of sodium, 4.2 wt % of phosphorus.

Catalyst H (Comparative Catalyst)

Preparation was carried out in a manner similar to catalyst F, except that calcination was carried out for 1 h at 650° C. and then for 1 h at 860° C. There was obtained a catalyst having a specific surface area of 1.2 $m^2/g$ and the following chemical composition: 89.5 wt % of cobalt, 5.1 wt % of manganese, 1.4 wt % of sodium, 4.2 wt % of phosphorus.

Catalyst 1 (Comparative Catalyst)

Preparation was carried out in a manner similar to catalyst F, except that calcination was carried out for 1 h at 820° C. only. There was obtained a catalyst having a specific surface area of 2.1 $m^2/g$ and the following chemical composition: 89.5 wt % of cobalt, 5.1 wt % of manganese, 1.4 wt % of sodium, 4.2 wt % of phosphorus.

Test Procedure

A vertical tubular reactor (diameter 16 mm; packed to a height of 50 cm; oil-heated double-walled jacket) was packed with 400 /g (200 mL) of a solid cobalt catalyst in the form of 4 mm extrudates. To effect reduction of the catalyst the temperature was increased in steps from 100° to 340° C. over a period of 24 h and then kept at 340° C. for 24 h, no pressure being applied while 200 L/h(STP) of hydrogen were passed through the reactor.

Through a tubular reactor (diameter 16 mm; packed to a height of 100 cm; oil-heated double-walled jacket) installed upstream of the hydrogenation reactor and packed with 37 g (50 mL) of titanium dioxide in the form of 1.5 mm extrudates, there were pumped upwardly at a pressure of 250 bar and a temperature of 80° C. 80 g/h of isophorone nitrile (purity 99.0%) and 270 g/h of liquid ammonia (throughput per unit catalyst 0.4 kg/L·h). There were then added, per hour, 100 L (STP)(4.5 mol) of hydrogen, and the effluent from the upstream imination reactor was passed upwardly through the hydrogenation reactor at a pressure of 250 bar and a temperature of 130° C. Following depressurization to standard pressure, the ammonia was removed by distillation and the hydrogenated effluent gas was analyzed chromatographically.

The results are listed in the following table:

| Catalyst | Hardness [N] (boiling test) | Surface Area [m²/g] | Aminonitrile [ppm] | Yield of isophorone diamine [%] |
|---|---|---|---|---|
| A | 20 | 1.6 | 200 | 99 |
| B | 21 | 3.2 | <100 | 99 |
| C | 11 | 15.1 | 200 | 99 |
| D | 19 | 3.0 | 200 | 97 |
| E | 15 | 6.2 | 400 | 99 |
| F | 0 | 7.1 | — | — |
| G | 16 | 1.4 | 600 | 99 |
| H | 3 | 1.2 | 700 | 99 |
| I | 1 | 2.1 | — | — |

What is claim is:

1. In a process for the preparation of a cobalt catalyst containing as catalytically active material from 55 to 98 wt % of cobalt, from 0.2 to 15 wt % of phosphorous, from 0.2 to 15 wt % of manganese and from 0.2 to 15% of alkali metal, calculated as oxide wherein the cobalt is precipitated from an aqueous solution of a water-soluble salt thereof by addition of an alkaline solution and then optionally spray-dried at an elevated temperature, and the phosphorous, manganese and alkali metal components are added during the cobalt precipitation or during the spray-drying step, and the resulting product after being dried is subsequently calcined at elevated temperatures, the improvement which comprises:

carrying out the calcination of the product in at least two steps, first at low temperatures of from 550° to 750° and thereafter at high temperatures of from 800° to 1000° C., each of the calcination steps being carried out for a period of time sufficient to produce a catalyst having a surface area of at least 1.5 m²/g and an abrasive hardness of at least 10 newton, as measured for the catalyst in its reduced form following a boiling test to determine its inertness to bases.

2. The catalyst obtained by the process of claim 1.

3. The catalyst obtained by the process of claim 1 and having a surface area of from 5 to 300 m²/g and an abrasive hardness of from 15 to 100 newton.

4. The catalyst obtained by the process of claim 1 and having a surface area of from 10 to 250 m²/g and an abrasive hardness of from 20 to 50 newton.

5. The catalyst obtained by the process of claim 1 which contains from 75 to 95 wt % of cobalt, from 0.5 to 10 wt % of phosphorous, from 2 to 10 wt % of manganese and from 0.5 to 5 wt % of alkali metal, calculated as oxide.

6. The catalyst obtained by the process of claim 1 in which the alkali metal is selected from the group consisting of lithium, sodium, potassium and cesium.

7. The catalyst obtained by the process of claim 1 in which the alkali metal is sodium.

8. The catalyst obtained by the process of claim 1 after reduction with hydrogen at an elevated temperature.

9. The catalyst obtained by the process of claim 8 after being placed in contact with hydrogen and with an organic compound selected from the group consisting of nitriles, imines and mixtures thereof at elevated temperatures and pressures.

* * * * *